(12) United States Patent
Turney et al.

(10) Patent No.: US 7,085,604 B2
(45) Date of Patent: Aug. 1, 2006

(54) MECHANICAL METAPHOR FOR REPRESENTING PARAMETER CONSTRAINTS GRAPHICALLY FOR MEDICAL DEVICES

(75) Inventors: Jerry L. Turney, Ramsey, MN (US); Yuemean Chen, Plymouth, MN (US); Scott Koelsch, Edina, MN (US); Kurt W. Papke, Chanhassen, MN (US)

(73) Assignee: Medtronic, Inc., Minneapolis, MN (US)

( * ) Notice: Subject to any disclaimer, the term of this patent is extended or adjusted under 35 U.S.C. 154(b) by 402 days.

(21) Appl. No.: 10/034,132

(22) Filed: Dec. 28, 2001

(65) Prior Publication Data

US 2003/0125776 A1      Jul. 3, 2003

(51) Int. Cl.
*A61N 1/36* (2006.01)

(52) U.S. Cl. .......................... 607/30; 607/60

(58) Field of Classification Search ............... 607/27, 607/4, 5, 29, 32, 59, 60, 88, 133, 105; 600/410, 600/411, 425, 427, 522, 523; 345/440, 440.2, 345/856, 858, 833, 859; 616/41
See application file for complete search history.

(56) References Cited

U.S. PATENT DOCUMENTS

| | | | |
|---|---|---|---|
| 4,476,868 A | | 10/1984 | Thompson ............ 128/419 PG |
| 4,811,256 A | | 3/1989 | Yamada et al. ............ 364/567 |
| 5,052,388 A | | 10/1991 | Sivula et al. ......... 128/419 PG |
| 5,188,105 A | * | 2/1993 | Keimel ............................ 607/5 |
| 5,292,341 A | * | 3/1994 | Snell ............................ 607/30 |
| 5,304,212 A | * | 4/1994 | Czeisler et al. ................ 607/88 |
| RE34,728 E | | 9/1994 | Hall-Tipping .......... 364/413.04 |
| 5,344,431 A | * | 9/1994 | Merritt et al. ................ 607/29 |
| 5,345,362 A | * | 9/1994 | Winkler ....................... 361/681 |
| 5,491,782 A | * | 2/1996 | King et al. .................. 345/833 |
| 5,615,347 A | * | 3/1997 | Davis et al. ................ 345/833 |
| 5,713,937 A | * | 2/1998 | Nappholz et al. ............. 607/30 |
| 5,724,985 A | * | 3/1998 | Snell et al. ................. 600/510 |
| 5,833,623 A | * | 11/1998 | Mann et al. ................. 600/523 |
| 5,940,293 A | | 8/1999 | Schwenke et al. ..... 364/167.07 |
| 6,031,547 A | | 2/2000 | Kennedy .................... 345/440 |
| 6,038,476 A | * | 3/2000 | Schwartz ..................... 607/27 |
| 6,061,062 A | | 5/2000 | Venolia ....................... 345/341 |
| 6,132,363 A | | 10/2000 | Freed et al. .................. 600/16 |
| 6,353,761 B1 | * | 3/2002 | Conley et al. ............... 607/28 |
| 6,515,665 B1 | * | 2/2003 | Ross .......................... 345/440 |
| 6,614,456 B1 | * | 9/2003 | Rzepkowski et al. ....... 345/833 |
| 6,748,276 B1 | * | 6/2004 | Daignault et al. ............ 607/46 |

OTHER PUBLICATIONS

Schildt, "More Common Controls," *MFC Programming From the Group Up*, p. 300-308 (1996).

* cited by examiner

*Primary Examiner*—Jeffrey R. Jastrzab
(74) *Attorney, Agent, or Firm*—Paul H. McDowall; Girma Wolde-Michael

(57) ABSTRACT

A system for representing parameter constraints that govern the values of interrelated parameters includes displays corresponding to a plurality of parameters having a range of values represented by a dimension in the displays. The interrelationship of the parameter constraints is maintained, when one or more of the displays change in value, by means of a software system to make an automatic adjustment while recognizing and maintaining the relationship between the parameters. The system is adjustable on a dynamic basis such that when a user adjusts the parameter either upwards or downwards the remaining interrelated parameters are simultaneously shifted to maintain constraints of the relationships consistent with prior condition before the change.

15 Claims, 8 Drawing Sheets

MECHANICAL METAPHOR FOR REPRESENTING PARAMETER CONSTRAINTS GRAPHICALLY FOR MEDICAL DEVICES

FIELD OF THE INVENTION

The present invention generally relates to medical devices. Specifically, the invention relates to the display of constraints to inform a user from entering values that may violate the constraints governing operational/functional parameters of the medical device.

BACKGROUND OF THE INVENTION

Constraining the values of a set of programmable parameters may generally confuse a user, particularly if the user does not understand how the constraints interact. Further, change in values or an entry of data that might violate the constraints would create problems. In various computer applications, particularly computer graphical systems, the interaction between parameters is usually shown using bar graphs.

For example, in U.S. Pat. No. 6,031,547 to Kennedy et al, a computer graphical status display for use in displays that monitor manufacturing processes, having a plurality of process parameters, provides a group of bar graphs placed in a side by side arrangement. The bar graphs are all scaled so that they have a common baseline value. When all process parameters are displayed at their baseline value, all graphs will have tops that are in alignment with the baseline. If a deviation of a graph beyond a predetermined threshold occurs, a visible warning section extending it in the baseline is displayed.

Similarly, U.S. Pat. No. 6,061,062 to Venolia et al, discloses a zooming controller. In accordance with this invention, when values are assigned to parameters, the mouse axes are made consistent with a positive or a negative change in that parameter's value. Thus, for values that need to be controlled more concisely, reducing the mouse's motion by some factor is preferred.

U.S. Pat. No. 5,940,293 to Schwenke et al, discloses a bar chart editor for an industrial controller. Specifically, the invention provides an editor apparatus and method for programming industrial controllers in relay ladder language. The apparatus or method used to provide RLL logic controls machine tools, movements in the desired sequence. The apparatus includes a display for creating a bar chart image that represents all functions in a cycle in graphically listed all function contingencies. The apparatus gleans function, cycle and contingency information from the image, and based on the information, creates modules that include logic required to make each function contingent upon illustrated conditions. A compiler then compiles the modules to provide an RLL program section to control the cycle.

U.S. Pat. No. RE34,728 to Hall-Tipping, discloses a video game difficulty level adjuster dependent upon players' aerobic activity level during the exercise. Primarily, this invention provides activity level signal along with a heart rate signal, incorporated in a video game such as Packman type video games. The game monitors the heart rate of the exerciser. If the heart rate falls outside preset minimum or maximum limits, a certain action occurs in the game such as an increase in the speed or skill level of the position. In the Packman type game, for example, should the heart rate fall below the desired workout rate, the villain would move at the speed faster than the player's speed, putting the player at a disadvantage. The player would respond by increasing his level of physical activities, thereby increasing the heart rate until it exceeds the minimum aerobic level required, at which time the villain's speed would return to its normal level.

U.S. Pat. No. 4,811,256 to Yamada et al, discloses input-output method and device for a combination of weighing system. Specifically, the invention relates to a combinational weighing system that requires a large number of parameters to be set for its operation. For some parameters, currently set values are displayed at the bar graph and the user can set or reset the value directly on the screen by moving a curser on the bar graph. Operating conditions can be changed in each cycle of the combinations of calculations at the top in the overall operation of the system.

U.S. Pat. No. 6,132,363 to Freed et al, discloses a cardiovascular support controlled system. In accordance with this invention, modification of parameters is done by double clicking on the desired parameter and adjusting the slider control or entering values directly. The default value is shown in square brackets and is always visible in the left corner of the slider bar window. Clicking on the OK button completes the adjustment of the local parameter table.

As it relates to medical devices, some programmable parameters, for example for a pacer or a defibrillator, are constrained by equality and inequality relationships. A user who does not understand the constraining values of a set of programmable parameters and the relationships thereof may be confused when a change in one value impacts the related set of parameters. It is therefore clear that a visual system indicating the interactive relationship between parameters, when one or more parameters are adjusted or varied, would be a very important training and evaluating tool for medical personnel and medical devices.

SUMMARY OF THE INVENTION

The present invention provides apparatus and method to show a user interactive relationship between constraints, and prevent the user from entering values that may violate the constraints. In a preferred embodiment, a mechanical method implementing sliders to display the interdependency of parameters based on the governing constraints is used.

One aspect of the invention provides a system for representing parameter constraints governing values of interrelated parameters when one or more of the parameters is changed. Specifically, the display includes a plurality of interrelated parameters, and a plurality of display corresponding to the plurality of parameters having a range of values represented by dimension of the displays and a software system that monitors and provides the interrelated parameter constraints when one or more of the plurality of displays undergo the change in value.

In yet another aspect of the invention, a system for adjusting related constraints on a dynamic basis is disclosed. The system includes a displayable metaphor including a plurality of sliders and a range of values implemented using the plurality of sliders and constraint means to maintain a constraining relationship for each of the plurality of sliders are disclosed. The plurality of sliders are interrelated parameters with dimension elements extending through slots or other dimensional elements with each position in the slot corresponding to a different value.

Yet another aspect of the invention relates to a method for representing parameter constraints for interrelated parameters of a medical device such as an implantable cardioverter defibrillator (ICD). The method includes providing a set of sliders slidable within a range of dimensions wherein each slider in a set represents an interrelationship. Further, the method includes imposing a constraint on each of the sliders representing the relationship, allowing a dynamic movement of the set of sliders to thereby represent a change in parameter value and constraining the set of sliders to change in correspondence with any change in one of the set of sliders.

Another aspect of the invention provides a representation of some of the programmable parameters for a medical device such as an ICD that are usually constrained by some mathematical relationships such as, for example, an inequality mathematical relationships. The invention allows a user to understand the interaction between the various parameters using a simple mechanical metaphor in addition to automatically adjusting and maintaining the relationship between the parameters when at least one parameter setting is changed by the user.

DETAILED DESCRIPTION OF THE PREFERRED EMBODIMENTS

Figure 1:
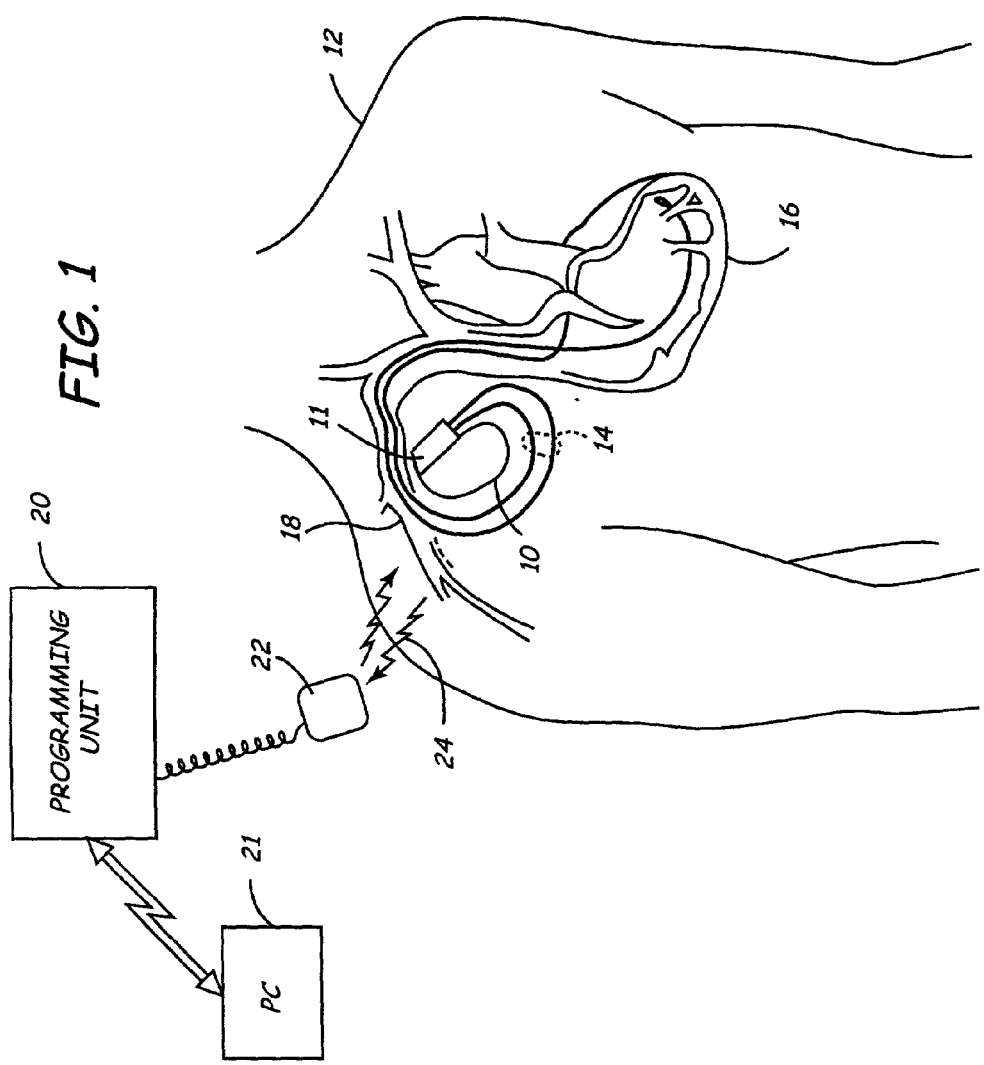
FIG. 1 is an illustration of a body implantable device system in accordance with one embodiment of the invention, including hermetically-sealed device implanted in a patient and an external programmer unit communicating with the implanted medical device.

FIG. 1 is an illustration of an implantable medical device system adapted for use in accordance with the present invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components, such as may occur during transtelephonic monitoring.

Also depicted in FIG. 1 is an external programming unit 20 for non-invasive communication with implanted device 10 via uplink and downlink communication channels 24, to be hereinafter described in further detail. Associated with programming unit 20 is a programming head 22, in accordance with conventional medical device programming systems, for facilitating two-way communication between implanted device 10 and programmer 20. Further, PC 21 is in wireless data communication with programmer 20. PC 21 could communicate with programmer 20 via a modem, telemetry or similar wireless data communication system, for example, to transfer displayable data to a remote location for review of displayed data by experts at a remote control site. In many known implantable device systems, a programming head such as that depicted in FIG. 1 is positioned on the patient's body over the implant site of the device, such that one or more antennae within the head can send RF signals to, and receive RF signals from, an antenna disposed within the hermetic enclosure of the implanted device or disposed within the connector block of the device, in accordance with common practice in the art.

Figure 2:
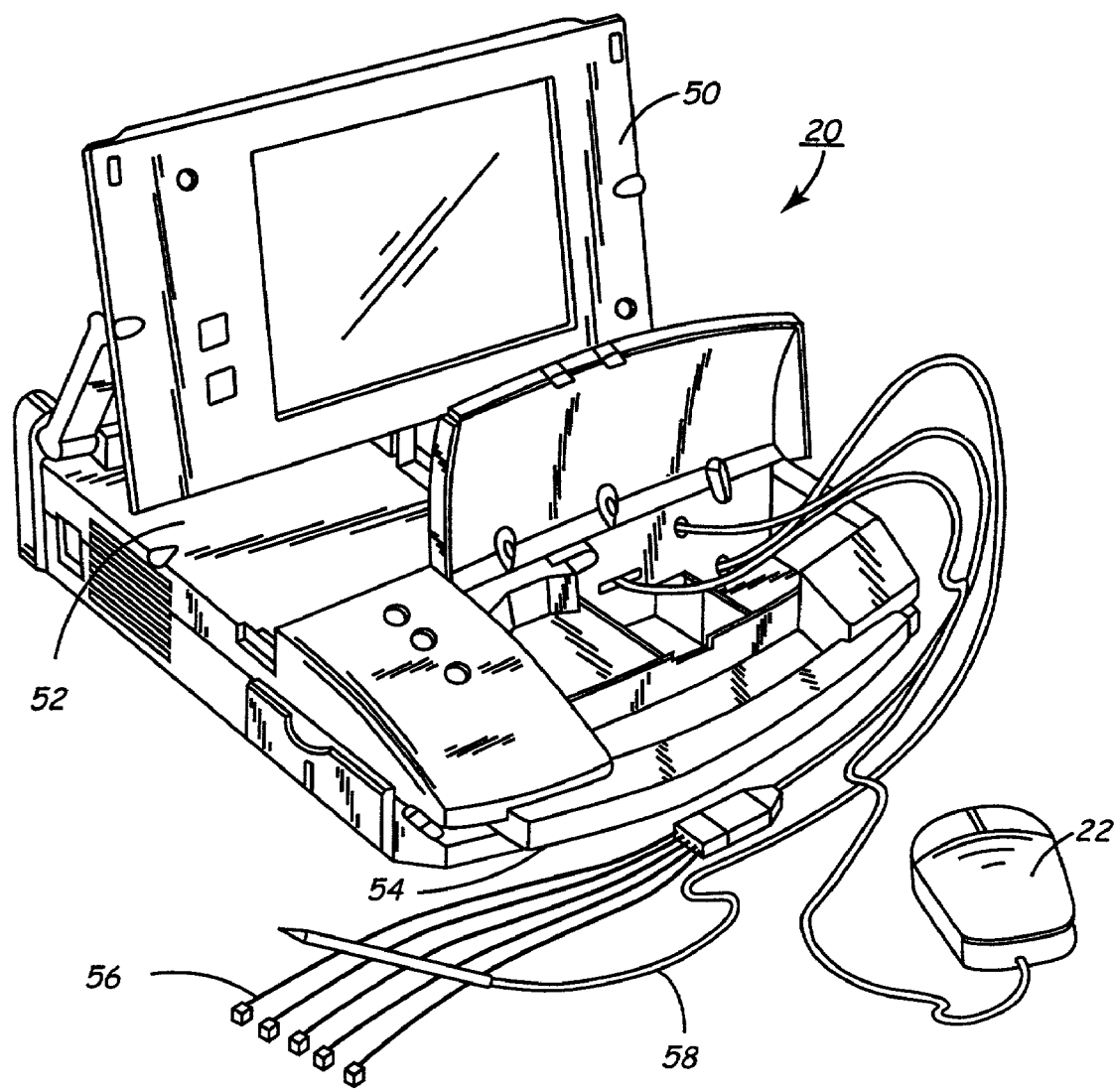
FIG. 2 is a view of the external programming unit of FIG. 1.

In FIG. 2, there is shown a perspective view of programming unit 20 in accordance with the presently disclosed invention. Internally, programmer 20 includes a processing unit (not shown in the Figures) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 52, which is preferably made of thermal plastic or another suitably rugged yet relatively lightweight material. A carrying handle, designated generally as 54 in FIG. 2, is integrally formed into the front of housing 52. With handle 54, programmer 20 can be carried like a briefcase.

An articulating display screen 50 is disposed on the upper surface of housing 52. Display screen 50 folds down into a closed position (not shown) when programmer 20 is not in use, thereby reducing the size of programmer 20 and protecting the display surface of display 50 during transportation and storage thereof.

A floppy disk drive is disposed within housing 52 and is accessible via a disk insertion slot (not shown). A hard disk drive is also disposed within housing 52, and it is contemplated that a hard disk drive activity indicator, (e.g., an LED, not shown) could be provided to give a visible indication of hard disk activation.

Those with ordinary skill in the art would know that it is often desirable to provide a means for determining the status of the patient's conduction system. Normally, programmer 20 is equipped with external ECG leads 54. It is these leads which are rendered redundant by the present invention.

In accordance with the present invention, programmer 20 is equipped with an internal printer (not shown) so that a hard copy of a patient's ECG or of graphics displayed on the programmer's display screen 50 can be generated. Several types of printers, such as the AR-100 printer available from General Scanning Co., are known and commercially available.

In the perspective view of FIG. 2, programmer 20 is shown with articulating display screen 50 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

Display screen 50 is operatively coupled to the computer circuitry disposed within housing 52 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
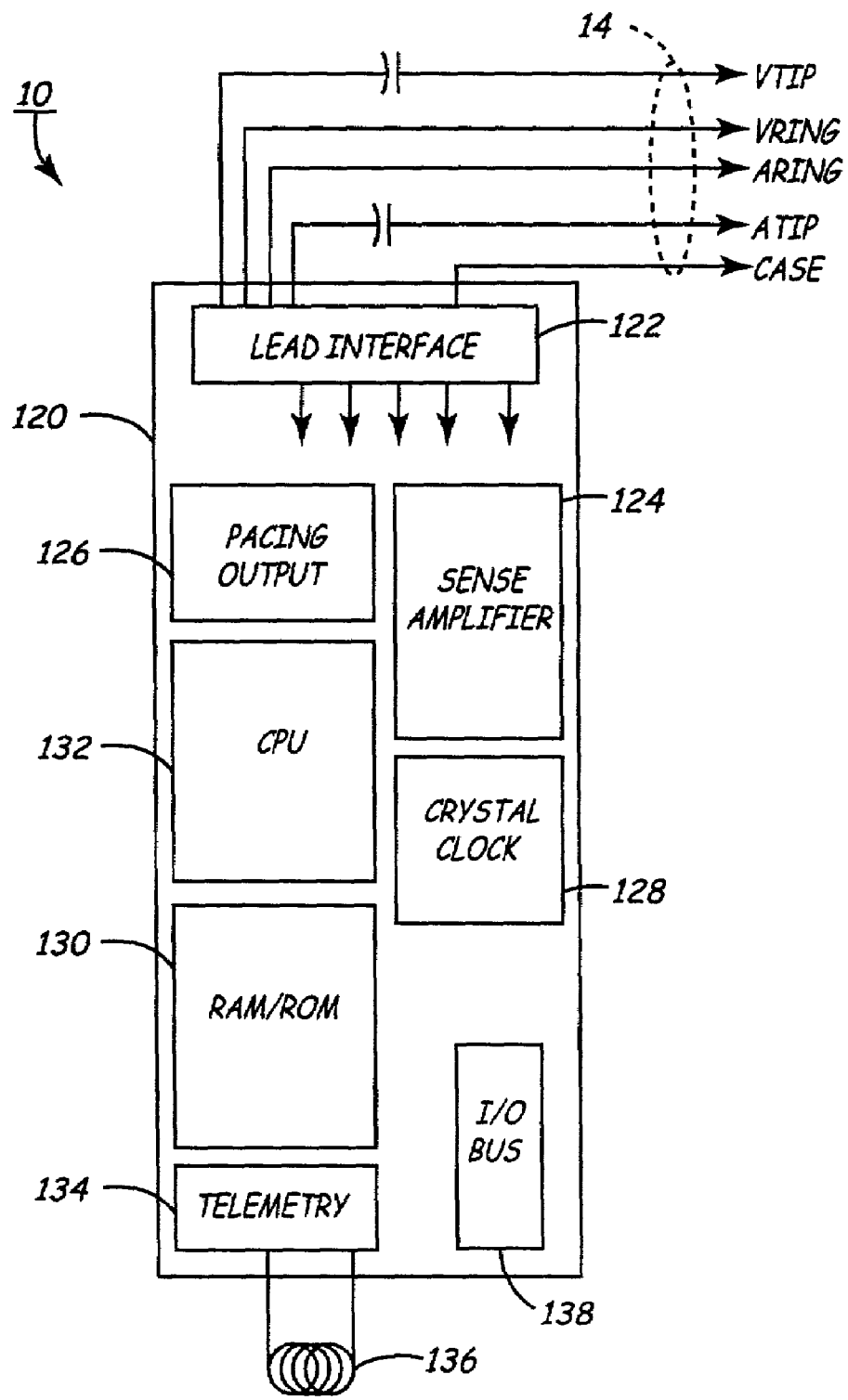
FIG. 3 is a block diagram of the implanted medical device system of FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 120 for controlling the device's pacing and sensing functions. The circuitry associated with stimulation control circuit 120 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 120 in FIG. 3 includes sense amplifier circuitry 124, stimulating pulse output circuitry 126, a crystal clock 128, a random-access memory and read-only memory (RAM/ROM) unit 130, and a central processing unit (CPU) 132, all of which are well-known in the art.

Pacemaker 10 also includes internal communication circuit 134 so that it is capable of communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 122 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 124 and stimulating pulse output circuit 126, in accordance with common practice, such that cardiac electrical signals may be conveyed to sensing circuitry 124, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 120 includes central processing unit 132 which may be an off-the-shelf programmable microprocessor or micro controller, but in the present invention is a custom integrated circuit. Although specific connections between CPU 132 and other components of stimulation control circuit 120 are not shown in FIG. 3, it will be apparent to those of ordinary skill in the art that CPU 132 functions to control the timed operation of stimulating pulse output circuit 126 and sense amplifier circuit 124 under control of programming stored in RAM/ROM unit 130. It is believed that those of ordinary skill in the art will be familiar with such an operative arrangement.

With continued reference to FIG. 3, crystal oscillator circuit 128, in the presently preferred embodiment a 32,768-Hz crystal controlled oscillator, provides main timing clock signals to stimulation control circuit 120. Again, the lines over which such clocking signals are provided to the various timed components of pulse generator 10 (e.g., microprocessor 132) are omitted from FIG. 3 for the sake of clarity.

It is to be understood that the various components of pulse generator 10 depicted in FIG. 3 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 126, which functions to generate cardiac stimuli under control of signals issued by CPU 132, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 124, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 132 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 134 in pacemaker 10, and an associated communication subsystem in external unit 20.

Figure 4A:
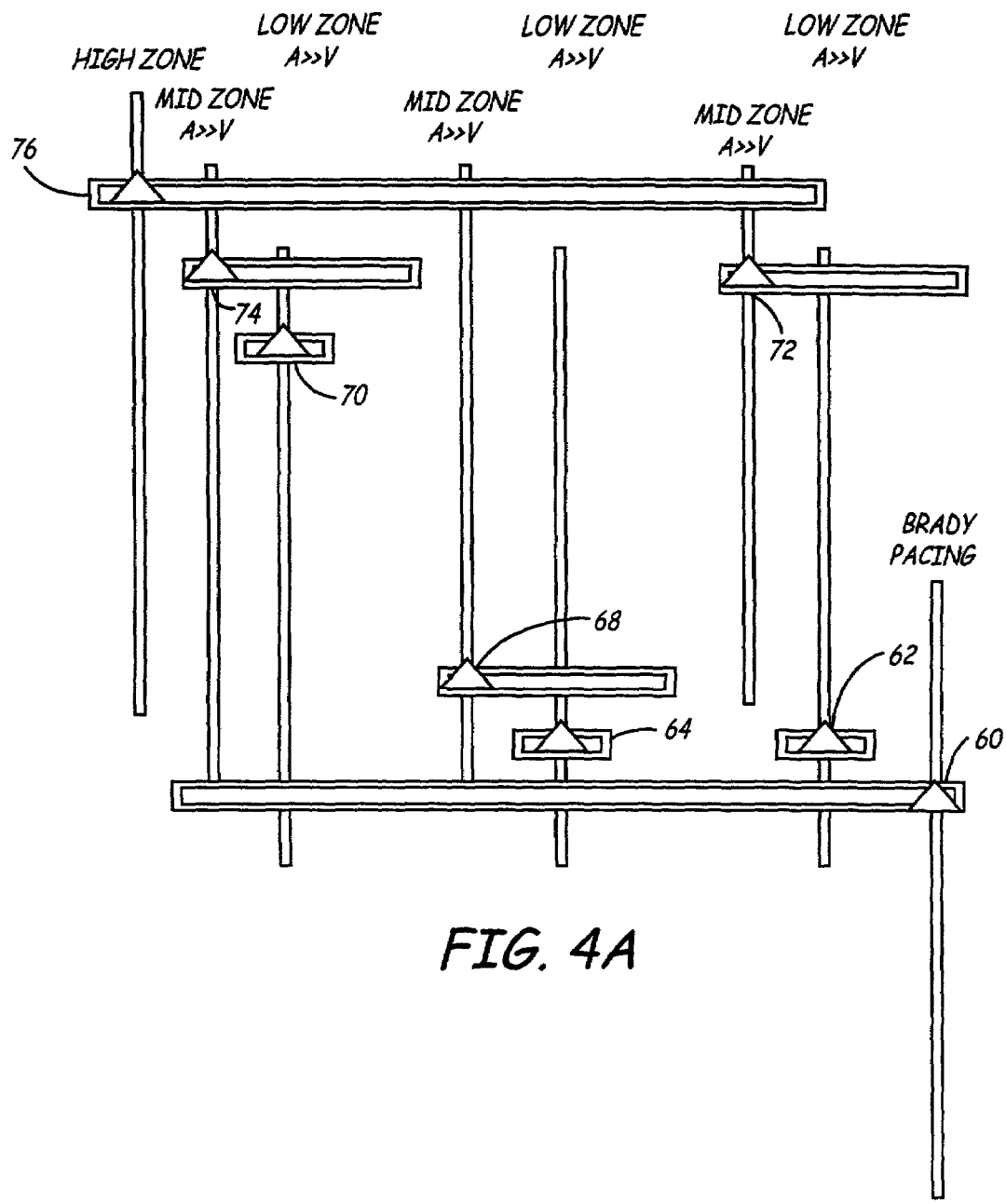
FIG. 4A is a representation of a display with parameter constraints indicated therein.

FIG. 4A represents parameter constraints depicted in accordance with the present invention. Slider 60 represents the parameters for Brady pacing. Slider 62 represents the parameters in the lowzone where atrial events are much higher than ventricular events. Similarly, slider 64 represents the lowzone where atrial events are equal to ventricular events. Slider 68 represents a midzone in which atrial events are equal to ventricular events. Slider 70 represents a lowzone where the atrial events are much less than the ventricular events. Slider 72 represents a midzone where the atrial events are much greater than ventricular events. Slider 74 represents a midzone condition in which atrial events are much less than ventricular events. Slider 76 represents a highzone.

Figure 4B:
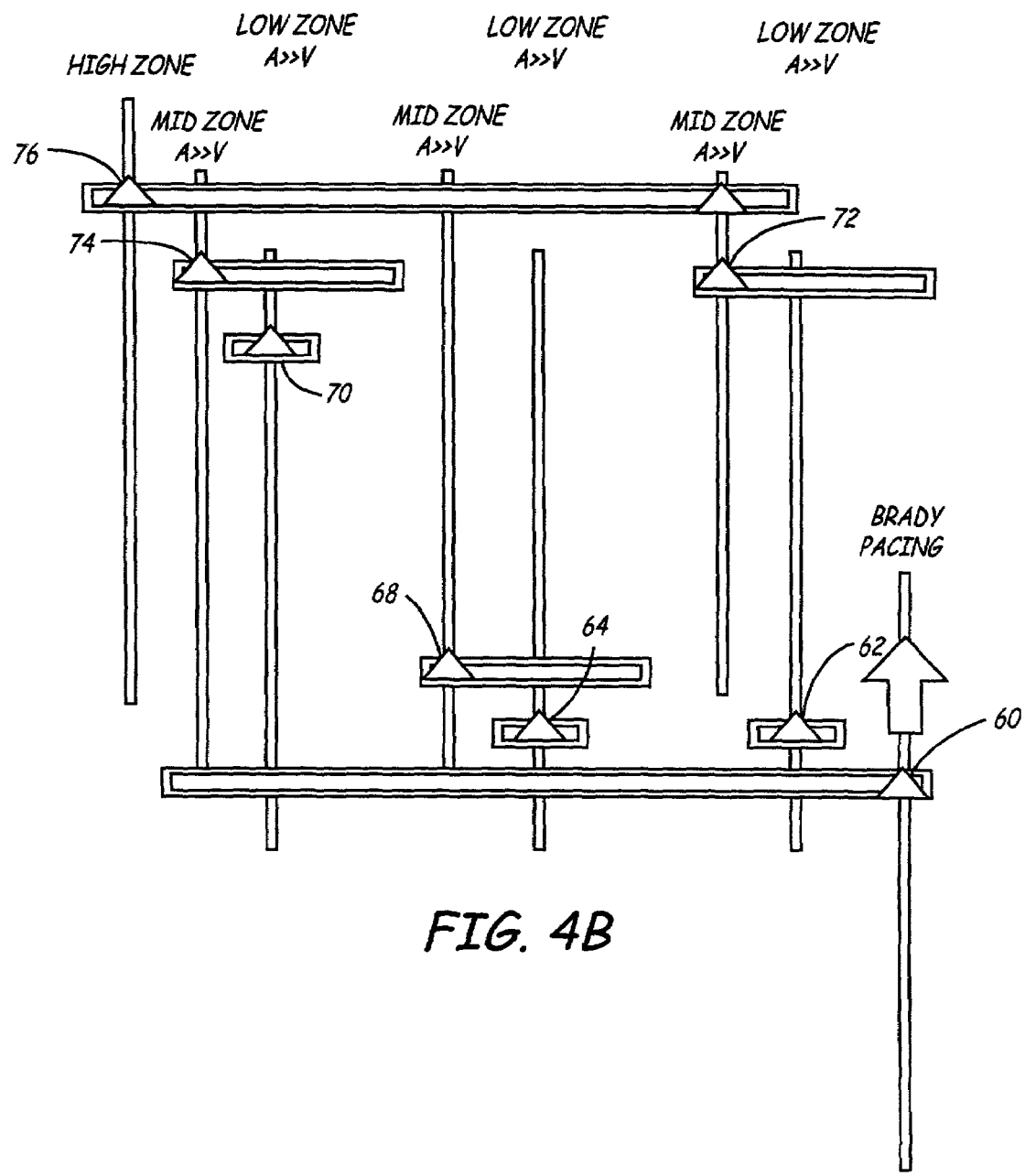
FIGS. 4B and 4C represent the display in FIG. 4A after one or more constrained values have been changed.
Figure 4C:
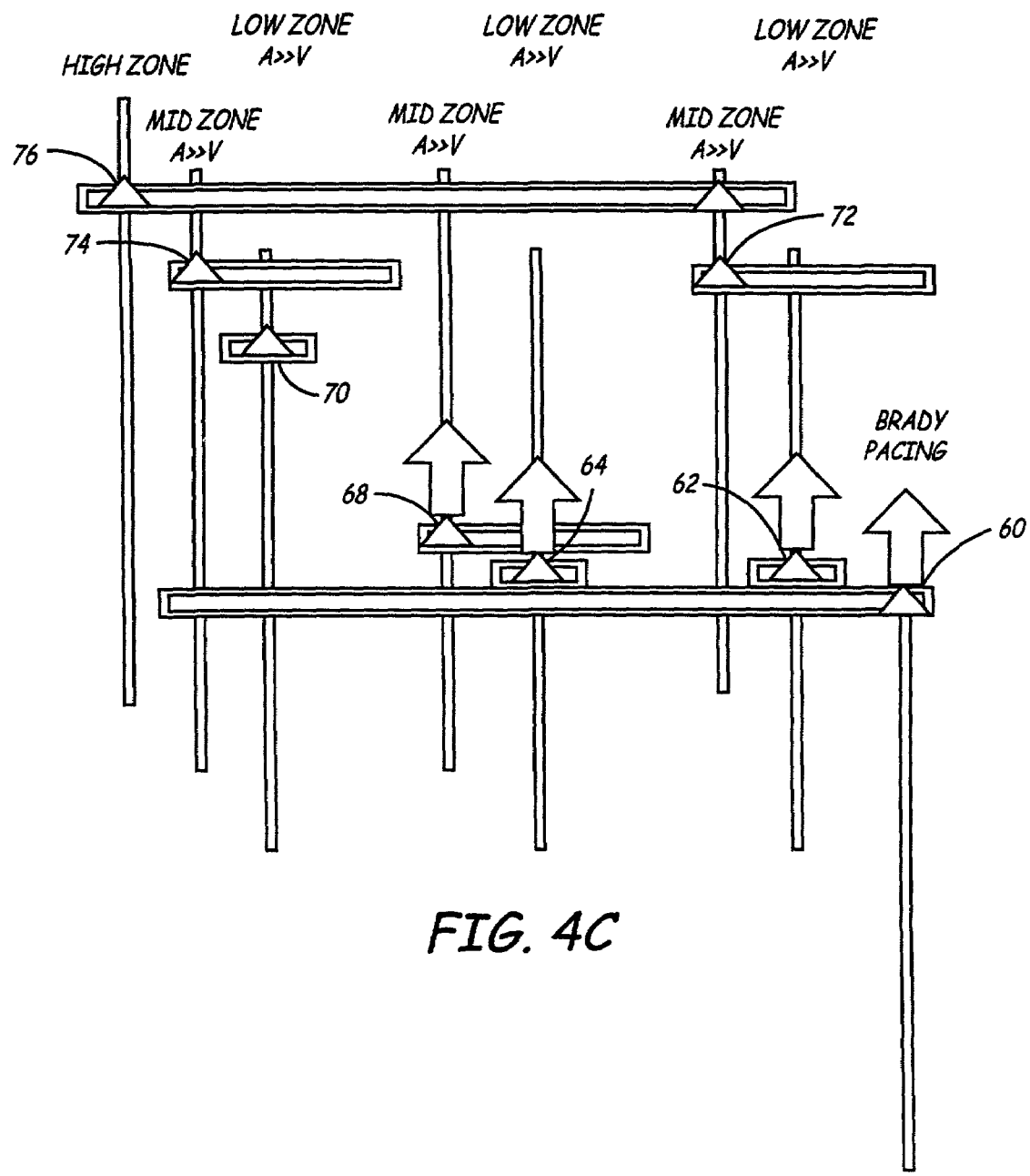

In accordance with FIG. 4A, if, for example, Brady pacing rate slider 60 were to be moved in an upward direction, it would cause all of the sliders immediately above it to also move upward thus preserving the inequality constraint. More specifically, with reference to FIG. 4B, when Brady pacing slider 60 is moved upward as indicated, all the other sliders move up correspondingly as indicated. Thus, in accordance to FIGS. 4B and 4C, changing the constraint value causes constraining values to change. Specifically, as shown in FIGS. 4B and 4C, a change in slider 60 results in changes that affect the related sliders.

Figure 4D:
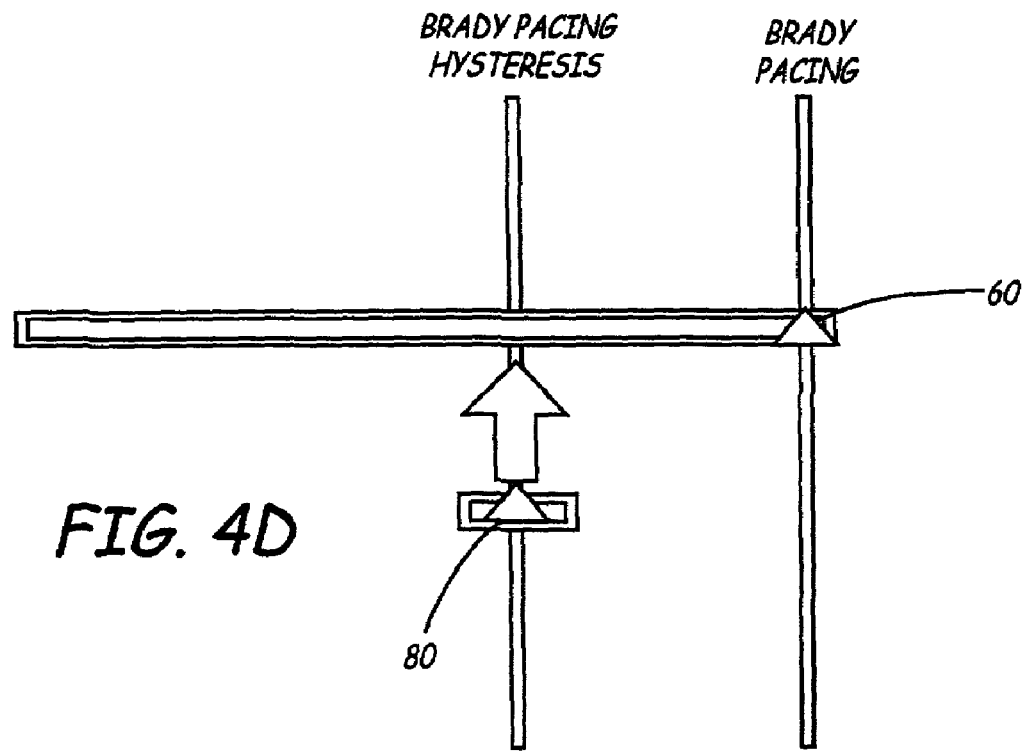
FIGS. 4D and 4E represent constraints having a greater than or equal to ($\geqq$) relationship and adjustments thereof.
Figure 4E:
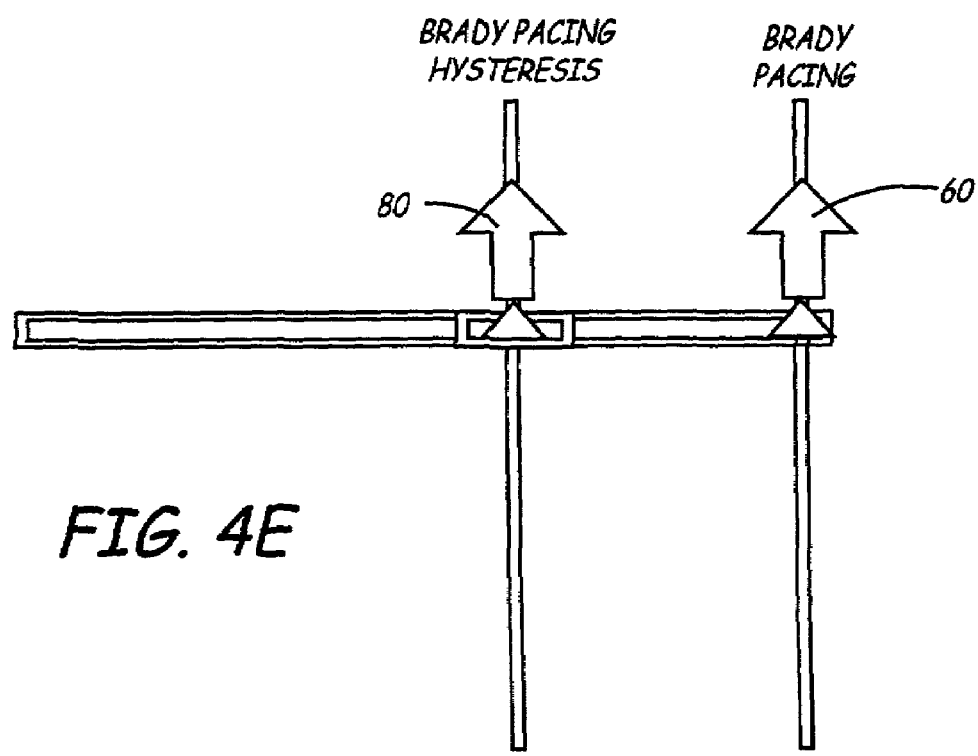

FIGS. 4D and 4E represent a case in which constraints are built around a greater than or equal to inequality. More specifically, in a Brady pacing situation slider 60 represents the Brady pacing rate and slider 80 represents Brady pacing hysteresis. As it stands, slider 60 is above slider 80 depicting the greater than segment of the relationship. However, if the equal to or greater than constraint is imposed and slider 80 moves upwards, the "equal to" relationship could be preserved and displayed.

Specifically, FIG. 4E depicts the process by which slider 80 is allowed to overlay constraining slider 60. Thus, Brady pacing hysteresis slider 80 is moved up and collides with its constraining slider Brady pacing rate slider 60. After the collision, the two sliders move upward together thereby exhibiting the greater than or equal to relationship.

Accordingly, the present invention provides the ability to set interrelated parameters in a medical device such as a dual chamber ICD or a pacemaker wherein a change in one related parameter could be reflected in corresponding changes in the other related parameters.

As indicated herein above, the sliders indicate the values of the interrelated parameters. The sliders have a range of values represented by their slot lengths. In other words, they are free to travel up and down the length of the slot with each position corresponding to a different value of the parameter. The sliders are also implemented to constrain one another based on a software system that maintains the constraining relationship within a given set of sliders. These sliders, unlike other user interface sliders include extensions that constrain the movement of other sliders that are related therewith. Thus, any movement of a slider would result in a corresponding movement of the other sliders consistent with the constraining relationship.

Figure 5:
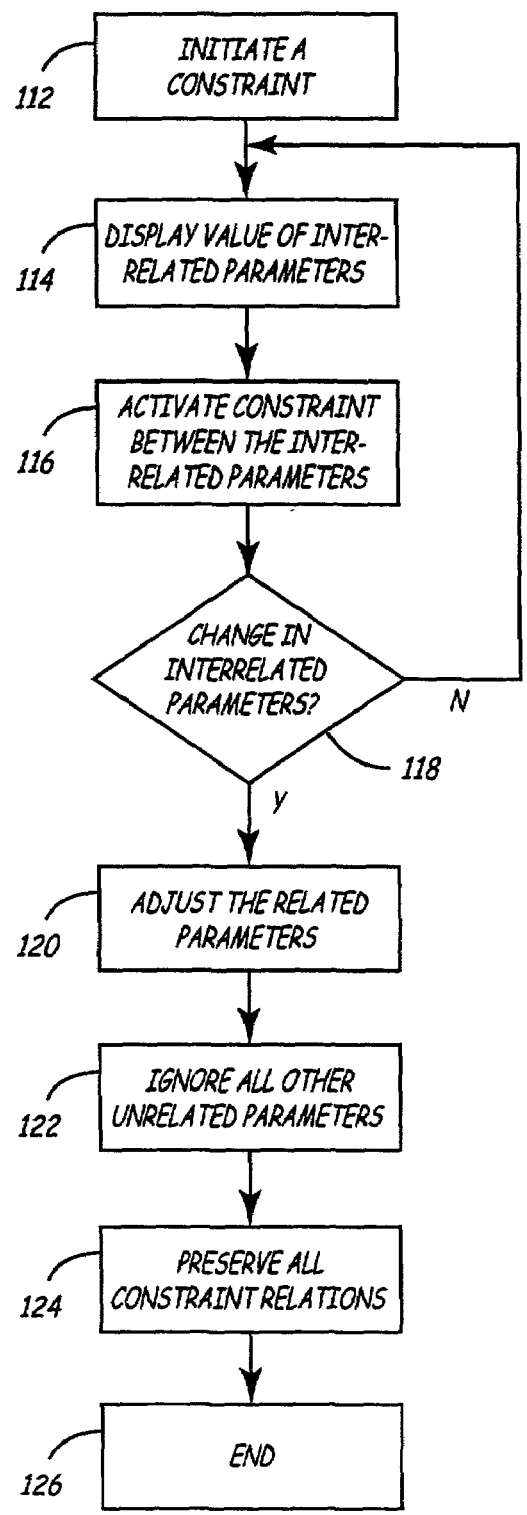
FIG. 5 is a flowchart depicting a high-level software logic implemented to maintain parameter relationship constraints in accordance with the present invention.

FIG. 5 is a simplified flowchart representing a high-level software logic implemented in the present invention. Specifically, software logic 110 is initiated at step 112 where the constraint system of the present invention is initiated. Under subsequent step 114 values of interrelated parameters are shown similar, for example, to the values depicted in FIGS. 4A, 4B and 4C. Subsequently, under step 116, the constraint between interrelated parameters is activated. Under logic step 118, the system logic checks whether there is a change in the interrelated parameters. In the even there is no change, the system logic reverts back to step 114, or in the alternate, may enter into a default mode routine to idle/wait until another command is initiated. If, however, there is a change in any of the interrelated parameters, the system proceeds to logic step 120 where any and all of the related parameters are adjusted to correspond to the change made in the parameter, thereby preserving the relationship. At step 122 all other unrelated parameters remain unchanged and the system logic retains them as is. While a change is effected, the constraint relationships that existed before the change is dynamically adjusted and preserved. Thus, the relationship between the interrelated parameters remains intact and the process ends at logic step 126.

While particular embodiments have been shown and described herein, it will be apparent to those skilled in the art that variations and modifications may be made in these embodiments without departing from the spirit and scope of this invention. It is the purpose of the appended claims to cover any and all such variations and modifications.

What is claimed is:

1. A system for setting interrelated operating parameters of an implantable medical device, the system comprising:
    a user interface having depictions of a plurality of interrelated operating parameters of an implantable medical device, the user interface depicting a range of values for each parameter wherein a dynamic change in one parameter is reflected in corresponding changes in the depiction of other parameters; and
    means for: (i) maintaining a constraining relationship between said interrelated operating parameters when one of the parameters is changed, (ii) ignoring all other unrelated parameters, and (iii) preserving the constraint relations that existed before the dynamic change occurred.

2. A system according to claim 1 wherein said plurality of interrelated operating parameters maintain a mathematical relationship with one another.

3. A system according to claim 1 wherein said interrelated operating parameters define an operationally stable performance envelope for the implantable medical device and wherein upon the adjustment of one of said plurality of interrelated operating parameters at least one other parameter of said interrelated operating parameters is modified.

4. A system according to claim 2 wherein a plurality of programmable constraints preserves the relationship by causing said plurality of interrelated operating parameters to consistently respond to a change in one of said plurality of interrelated operating parameters.

5. The system of claim 1 wherein a change in a constrained parameters causes at least one other constraining parameter to change.

6. A method for setting interrelated operating parameters of an implantable medical device (IMD), the system comprising:
    depicting upon a user interface a plurality of interrelated operating parameters of an implantable medical device (IMD) including a range of values for each interrelated operating parameter wherein when a dynamic change occurs in one parameter the dynamic change is reflected in corresponding changes in the depiction of other parameters;
    maintaining a constraining relationship between said interrelated operating parameters when one of the parameters is changed;

ignoring possible changes to each parameter that does not include a constraining relation with one of the parameters is changed; and preserving the constraint relations that existed before the dynamic change occurred.

7. A method according to claim 6, wherein said plurality of interrelated operating parameters maintain a mathematical relationship with one another.

8. A method according to claim 7, wherein a plurality of programmable constraints preserves the relationship by causing said plurality of interrelated operating parameters to consistently respond to a change in one of said plurality of interrelated operating parameters.

9. A method according to claim 6, wherein said interrelated operating parameters define an operationally stable performance envelope for the implantable medical device and wherein upon the adjustment of one of said plurality of interrelated operating parameters at least one other parameter of said interrelated operating parameters is modified.

10. A method according to claim 6, wherein a change in a constrained parameters causes at least one other constraining parameter to change.

11. A computer readable medium encoded with executable instructions for setting interrelated operating parameters of an implantable medical device (IMD), the medium comprising:

executable instructions encoded into a computer readable medium for depicting upon a user interface a plurality of interrelated operating parameters of an implantable medical device (IMD) including a range of values for each interrelated operating parameter wherein when a dynamic change occurs in one parameter the dynamic change is reflected in corresponding changes in the depiction of other parameters;

executable instructions encoded into the computer readable medium for maintaining a constraining relationship between said interrelated operating parameters when one of the parameters is changed;

executable instructions encoded into the computer readable medium for ignoring possible changes to each parameter that does not include a constraining relation with one of the parameters is changed; and executable instructions encoded into the computer readable medium for preserving the constraint relations that existed before the dynamic change occurred.

12. A computer readable medium according to claim 11, wherein said plurality of interrelated operating parameters maintain a mathematical relationship with one another.

13. A computer readable medium according to claim 12, wherein a plurality of programmable constraints preserves the relationship by causing said plurality of interrelated operating parameters to consistently respond to a change in one of said plurality of interrelated operating parameters.

14. A computer readable medium according to claim 11, wherein said interrelated operating parameters define an operationally stable performance envelope for the implantable medical device and wherein upon the adjustment of one of said plurality of interrelated operating parameters at least one other parameter of said interrelated operating parameters is modified.

15. A computer readable medium according to claim 11, wherein a change in a constrained parameters causes at least one other constraining parameter to change.

* * * * *